(12) United States Patent
Souney et al.

(10) Patent No.: US 6,478,740 B2
(45) Date of Patent: Nov. 12, 2002

(54) PORTABLE HAND-CARRY SATELLITE DIAGNOSTIC ULTRASOUND SYSTEM FOR GENERAL AND CARDIAC IMAGING

(75) Inventors: Sean Souney, 230 Madeline Dr. Lincoln Ave., Pasadena, CA (US) 91105; Richard W. Roeder, Tustin, CA (US)

(73) Assignee: Sean Souney, Pasadena, CA (US)

( * ) Notice: Subject to any disclaimer, the term of this patent is extended or adjusted under 35 U.S.C. 154(b) by 0 days.

(21) Appl. No.: 09/964,722

(22) Filed: Sep. 26, 2001

(65) Prior Publication Data

US 2002/0040186 A1 Apr. 4, 2002

Related U.S. Application Data

(60) Provisional application No. 60/235,481, filed on Sep. 26, 2001.

(51) Int. Cl.[7] ................................................. A61B 8/00
(52) U.S. Cl. .......................................................... 600/437
(58) Field of Search ................................. 600/437, 438, 600/443, 459, 460

(56) References Cited

U.S. PATENT DOCUMENTS 5,758,649 A * 6/1998 Iwashita et al. ............. 600/459
5,984,880 A * 11/1999 Lander et al. ............... 600/595

* cited by examiner

*Primary Examiner*—Francis J. Jaworski
*Assistant Examiner*—Maulin Patel

(57) ABSTRACT

An ultrasound imaging system 18 for the generation of image data at a first location 16 that sends said data to a main ultrasound diagnostic imaging machine 10 for processing or viewing of the image data. The data may be processed up to the capabilities of the main machine 10 and then formatted in the format capabilities of the main machine 10 (duplex scan, color enhanced images, etc.) where the digital data can be sent via hard wire or wireless transmission to a network for viewing (image or processed data) or to the portable hand carry satellite ultrasound imaging machine.

1 Claim, 2 Drawing Sheets

PORTABLE HAND-CARRY SATELLITE DIAGNOSTIC ULTRASOUND SYSTEM FOR GENERAL AND CARDIAC IMAGING

This application claims the benefit of U.S. provisional Application No. 60/235,481, filed Sep. 26, 2001.

FEDERALLY SPONSORED RESEARCH

Not Applicable

SEQUENCE LISTING OR PROGRAM

Not Applicable

BACKGROUND—Field of Invention

This invention relates to diagnostic ultrasound, specifically to the machinery and the software processes that allow data processing and communication of the processed data between the main ultrasonic diagnostic imaging machine (UDIM) and the portable hand carry satellite (peripheral) imaging machine.

BACKGROUND—Description of Prior Art

Patients requiring diagnostic ultrasound must be physically brought to the large wheeled ultrasonic imaging machine or the large wheeled ultrasonic imaging machine must be physically brought to the patient's bedside. The smallest of the units which are able to process image information into diagnostic information, i.e. duplex scanning (spectral doppler imaging) and that have features which are diagnostic in nature, i.e. color flow imaging, three dimensional imaging, etc. is over three hundred pounds and still must travel in a specially made van between hospitals and requires large very expensive crates when moved by rail or plane.

The reason for this is that the amount of data that is processed is great and even with the advances in surface mount electronics, microelectronics and wireless technology, the current data processing capabilities of these units which include features such as duplex scanning (spectral doppler) can not be miniaturized to the point that they will fit in a hand held unit and generate the data processing and analysis to make the digitized image of any value to a physician, other than the image itself and basic command functions that a coupled medical diagnostic imaging system can have with an ultrasound peripheral.

U.S. Pat. No. 5,891,035 discloses an imaging system capable of accessing images and information from internal or external databases by means of a browser. This access may be over a local network or over a worldwide network such as the Internet. The browser may be used to pull in system preset data or reference images from a reference image library. This only helps as a comparative visual reference to an image that one may request to view in relation to a live image currently being viewed.

U.S. Pat. No. 5,384,494 describes the ability of an ultrasound system to control via wireless command the peripheral system and U.S. Pat. No. 6,120,447 deals with image transmission through the use of a computer and routing device.

None of the above mentioned patents describe the invention and its software processes which allow the satellite imaging unit to essentially function at the same level of data processing complexity as the host UDIM.

OBJECTS AND ADVANTAGES

Accordingly, the objects and advantages of the present invention are:

(a) to provide a satellite ultrasonic imaging machine that is hand carried and has the ability of sending the ultrasonic image data by digitally compressing it and sending it to the main UDIM for processing and then returning the processed data which will give complex information which includes but is not limited to duplex scanning (spectral doppler) images or statistical data related to the ultrasonic image.

(b) To provide a motorized mechanical transducer probe the movement of said probe can be commanded or moved (linearly or rotated) about an area which it has circumscribed on a limb or body part allowing movement commands from a main UDIM to change viewing images at a peripheral site through probe movements.

(c) the use of a satellite device of this type allow complex scans to be received after their image data is processed with a portable device allowing rapid response time to physicians requests and greater flexibility in scheduling time (time and cost savings).

(d) The reduction of liability to the patient and the main UDIM because, again, neither the patient has to be moved to the UDIM or vice versa.

(e) The technical training level of the application specialist can be reduced (f) The treatment time can be minimized due to its simplified application.

(g) the relief of the highly trained and limited number of RVT's and/or physicians at the main UDIM of difficult and many times impossible travel and setup time at the patient's location.

(h) The extremely difficult physical problems of transporting a large piece of equipment to the patient's bedside are negated.

(i) Complex imaging and data processing features are available at any location that a hand carried unit can travel (emergency field rescues, home or job site emergencies).

(j) The patient is more content and less anxious because of the improved convenience.

(k) The diagnosis is completed rapidly and at less expense, with a greater and more complex analysis which would reduce patient mortality and long term treatment of venous and arterial illnesses.

(l) With the reduction of educational requirements of the ultrasound technician ( as the data can be processed by anyone in real time or at a later time) transport/setup time are reduced and overall treatment costs are reduced.

(m) Features such as high definition imaging, color pulsed doppler, greater than 256 gray shade 2 dimensional imaging, color values from a 24 bit pallete, digital coherent processing(phase and amplitude information to optimize resolution and frame rate), and spectral doppler processing are accessible on the screen of the peripheral unit.

(n) because of the portability of our satellite unit, accurate and complex venous screening for Deep Vein Thrombosis (Venous thromboembolism) and the resultant life threatening pulmonary embolism before surgery and throughout the patients risk period can now be performed at minimal cost and time and with lifesaving results whereas now this type of screening is avoided entirely for logistical and financial reasons.

Still further objects and advantages will become apparent from a consideration of the ensuing description and drawings.

SUMMARY

In accordance with the present invention a portable hand-carry satellite diagnostic ultrasound system for general and cardiac imaging comprises an ultrasound imaging machine, a satellite monitor which contains a CPU to digitize data for transmission, a satellite sending/receiving unit which functions as an airport for wireless or hardwire transmissions, and a main UDIM machine which also has a sending/receiving unit attached to the probe interface for the transmission or reception of wireless or hardwired data to or from the UDIM.

DRAWINGS

Drawing Figures

In the drawings, closely related figures have the same number but different alphabetic suffixes.

REFERENCE NUMERALS IN DRAWINGS

| | |
|---|---|
| 10 main UDIM (Ultrasonic diagnostic imaging machine) | 12 base station for receiving/sending transmissions of data |
| 14 probe transducer motorized | 16 patient |
| 18 hand carried portable ultrasonic imaging machine | 20 imaging technician |
| 22 probe tranducer manual | 24 display monitor |
| 26 transducer probe hardwire connection | 28 sending or receiving port (wireless or hardwired) |
| 30 satellite sending/receiving unit | 32 connection to UDIM probe |

DETAILED DESCRIPTION

Figure 1A:
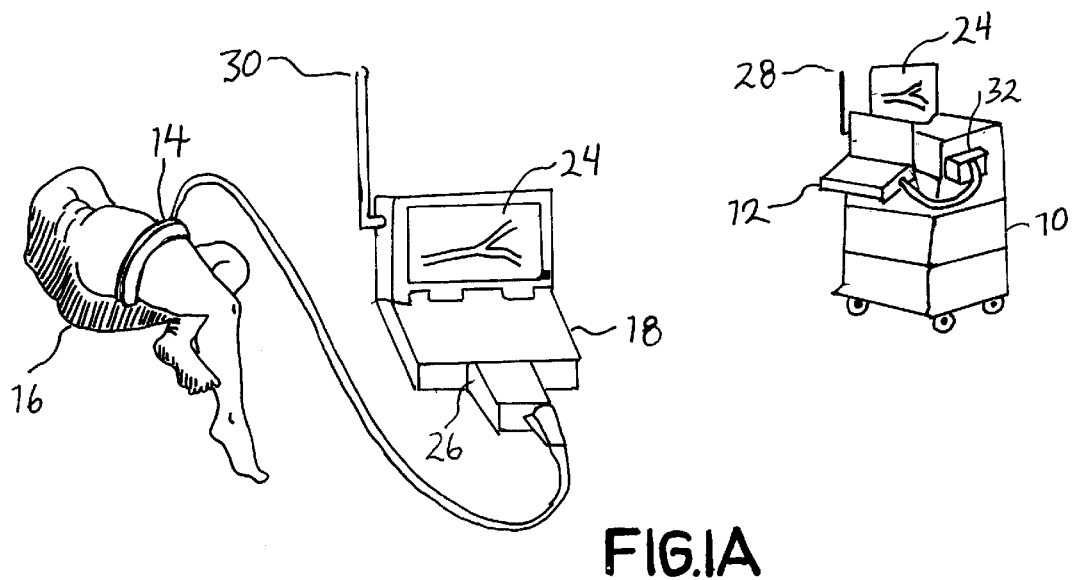
FIGS. 1A and 1B show the main aspects of the hand carried satellite ultrasonic imaging machine in relation to the main Ultrasonic Diagnostic Imaging Machine (UDIM) shown both with a manual and a motorized transducer probe.
Figure 1B:
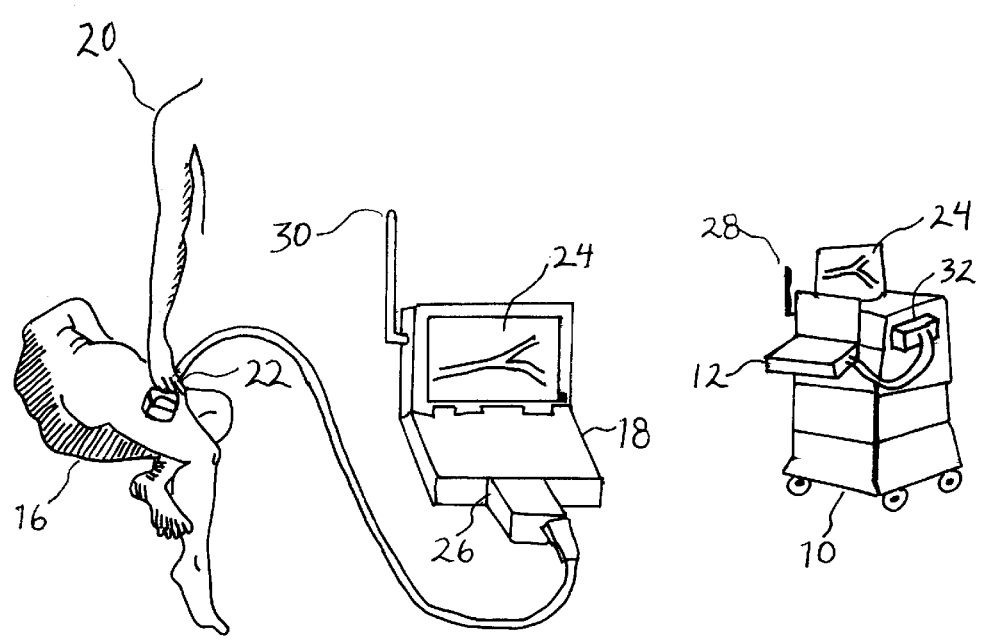

DESCRIPTION—FIGS. 1A and 1B—Preferred Embodiment

A preferred embodiment of the hand carried portable satellite diagnostic ultrasound system (PSDUS) is illustrated in FIGS. 1A and 1B. The PSDUS is attached to a portable Central processing unit which is a computer which is responsible for taking the images from the probe, digitizing them and compressing them so they can be sent via the airport by wireless or hardwire transmission to the main UDIM where the data is processed and can then be resent to the PSDUS in a format where the data has been processed, the image enhanced or selectively processed (duplex scanning values or graphs). At the main UDIM, where the data processing takes place there is a sending and receiving unit that works at the probe interface. Data is formatted to be acceptable and duplicate the process of data transmission as if there were the standard transducer probe sending the data back after the sonic penetration.

Duplex imaging and statistical analysis are only several of the higher level processing functions that these machines perform. The smaller units for imaging process only imaging data. The data is the same when digitized as the processed data from the larger UDIM which with the current technology of streaming video and airports (wireless data transmission) can be processed by the larger unit and sent for viewing by the smaller PSDUS unit. This enables a technician to actually take the readings with anatomical landmark knowledge and see the probe location. Slight rotations or movements can either be accomplished by commanding a motorized (mechanical) transducer probe or instructing the movement since at the main UDIM the image seen by the technician can be viewed in real time.

Assessment of the data received at the main UDIM can begin and analysis (duplex scanning or other important data) can be finished at the main UDIM. A physician or higher level RVP technician working with the portable unit may require the analysis at the patient's bedside. The processed data is requested and sent down to the portable from the main UDIM after processing. Even simple processing functions like increased resolution now give the satellite handheld unit a higher quality visual at the limits of the monitor quality because the channel inputs received from the handheld unit have more refinement in their signal processing in the main UDIM.

Advantages

From the description above, a number of advantages of the present invention become evident:

(a) The portable satellite hand carried ultrasonic imaging machine has the ability of processing the ultrasonic image data by digitally compressing it and sending it to the main UDIM for processing and then returning the processed data in the requested format (example: a duplex scanned image with a statistical average of ten flow measurements) which will give complex information which includes but is not limited to duplex scanning of images or statistical data processing related to the ultrasonic image information.

(b) since digitized information can be sent between the units, the possibility of a mechanized transducer probe that could be placed over a general anatomical landmark, would allow a technician at the main UDIM to control the placement of the transducer probe at a location away from the main UDIM since the technician is able to view the information sent from the portable hand carried satellite ultrasonic imaging system. Exact placement from server motor movement of the transducer probe through this command function would require less technical expertise on the part of the technician at the bedside.

(c) the use of a satellite device means that travel time to wheel the heavy main UDIM to the bedside is reduced. More rapid response time and the ability to take the image from the portable unit and send the data (image) for storage and eventual processing makes physician's time more flexible and results in both time and cost savings.

(d) the liability to the patient ( maybe not receiving the scan) and the main UDIM (movement of a large machine translates to wear and breakage) is reduced since neither the patient nor the UDIM need be moved.

(e) the application specialists training can be reduced.

(f) the treatment time can be minimized due to the simplified portable machine operation (g) now complex data analysis and not merely the interpretation of a grayscale image are available at any location that a hand carried portable unit can travel.

(h) the patient is more content and less anxious because of the improved convenience.

(i) the diagnosis is completed more rapidly and at less expense with a greater and more complex analysis which would reduce patient mortality and long term treatment of venous and arterial illnesses.

(j) With the reduction of the educational requirements of the ultrasound technician and the expediency of the setup time costs to the hospitals and the patients are reduced.

(k) Features such as high definition imaging, color pulsed doppler, greater than 256 gray shade two dimensional imaging, color values from a 24 bit pallette and digital coherent processing (phase and amplitude information to optimize resolution and frame rate).

(l) Accurate and complex venous screening for Deep Vein Thrombosis (venous thromboembolism) and the resultant life threatening pulmonary embolism (PE) can now be performed on more patients at minimal cost and time with lifesaving results whereas now this type of screening is avoided entirely for logistical and financial reasons.

Operation

Figure 2A:
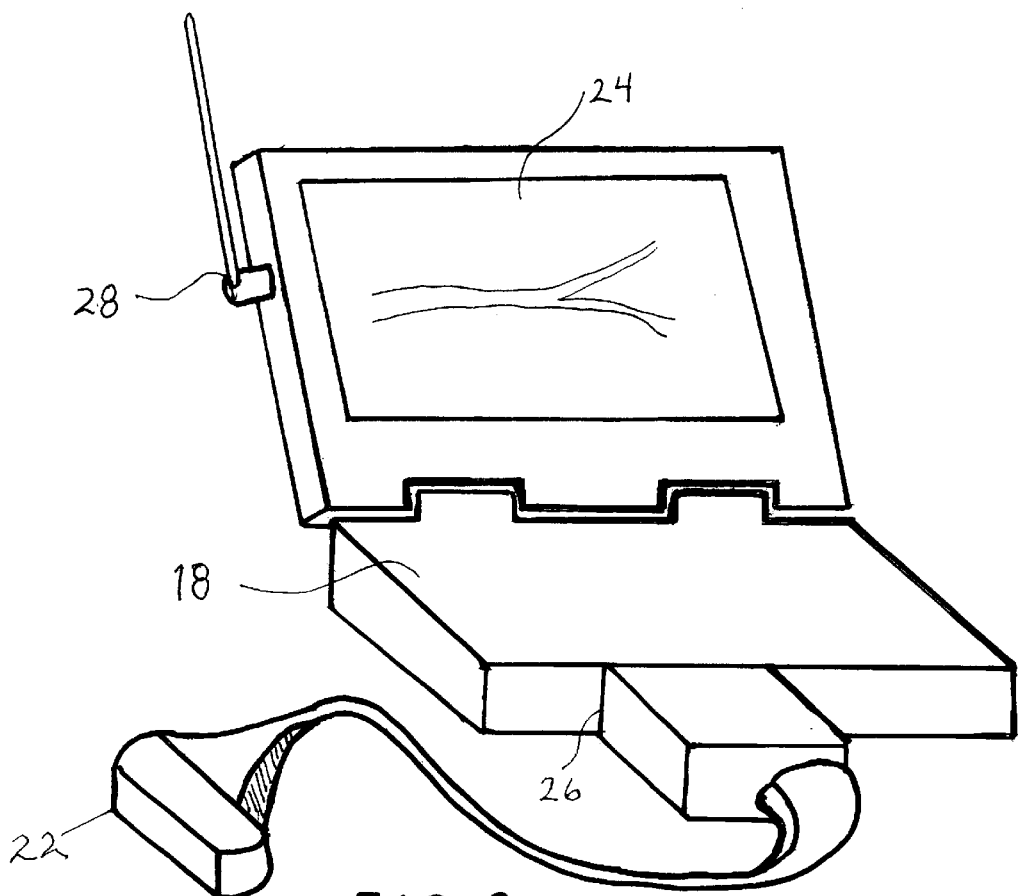
FIGS. 2A and 2B show the hand-carried portable satellite ultrasonic imaging machine and satellite sending/receiving unit which are used to move the data between the two machines (portable and main ultrasonic imaging machine).
Figure 2B:
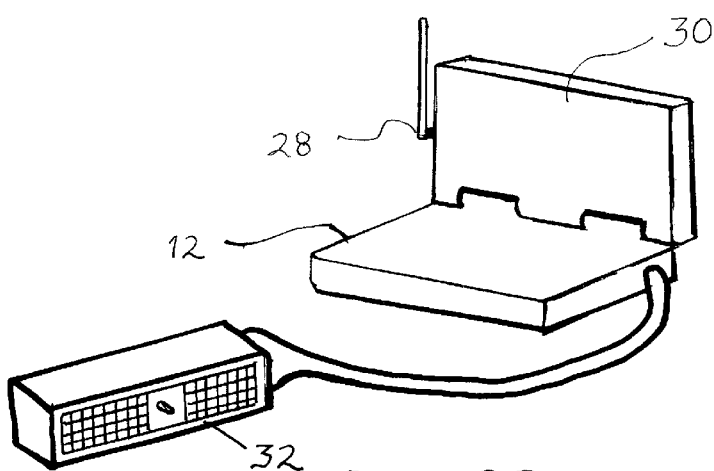

FIGS. 1 and 2 show the 18 hand carried portable ultrasonic imaging machine with its 26 connection which because of electrical signals is not capable of being wireless. The 28 sending/receiving port is responsible for wireless or hard T3 communications wiring transmission or reception of the data signals to and from the main UDIM and in the 30 satellite sending/receiving unit at the main UDIM 10. The satellite sending/receiving unit 30 is called a 12 base station because its power of transmission must be higher than the sending port 28 on the 18 hand carried portable ultrasonic imaging machine.

To operate, the technician with a transducer probe connected to the satellite unit generates an image of blood moving in a vein. The image is clear and in the correct viewing format to gather some complex diagnostic data such as a spectral doppler image. An interval of viewed time of the vein is then sent as digitized information to the main UDIM which is manned by a technician which takes the image data and processes it into a spectral doppler image (a duplex scan), the technician at the bedside commands that this processed data be sent to the bedside portable satellite ultrasonic imaging machine. The image then is transmitted and at bedside with a strictly imaging device can now view more diagnostic information for assessment and make a decision. This information is also viewable by the physician which could be stationed at the main UDIM which prevents his/her movement to the bedside or the information could be sent to a network where it could be accessed or downloaded at the physicians office for example. This has numerous advantages which are noted above.

CONCLUSION, RAMIFICATIONS, AND SCOPE

Accordingly, the reader will see the portable hand carried satellite diagnostic ultrasound system for use in conjunction with a standard 128 or more channel main ultrasound system with complex data processing features such as duplex scanning technology is an important invention for the health industry as is will bring a major diagnostic tool to more bedsides because of its portability and reduce the cost of treatment as the main ultrasonic machine will not have to be transported to the bedside and minimal training will be needed to scan with the portable unit allowing many more people the use of this diagnostic tool in the hospital and in the field.

We claim:

1. In an ultrasound imaging system for generating image data at a first location in response to scanning of a subject under study, an improved apparatus for processing the transmitted data and transmitting the processed data comprising in combination of:

a computer connected to the portable satellite hand carried ultrasonic imaging machine a network interface connected to the portable satellite hand carried ultrasonic imaging machine and computer that includes an air port function (network transmit module and network receive module) for the transmission and reception of data to and from the main ultrasound diagnostic imaging machine (UDIM)

a network interface connected to the main ultrasound diagnostic imaging machine (UDIM) that includes an air port function (network transmit module and network receive module) for the transmission and reception of data to and from the portable satellite hand carried ultrasonic imaging machine an asynchronous network for transmitting the received data via an internet protocol, whereby image data generated by the hand carried portable ultrasound imaging system may be transmitted with or without wires to a network before storage or to main UDIM where the image data may be processed or refined and then transmitted back to the portable satellite hand carried ultrasonic imaging machine or to a network before storage.

* * * * *